United States Patent [19]

Gordon et al.

[11] Patent Number: 4,743,539

[45] Date of Patent: May 10, 1988

[54] SPECIFIC ANTIBODY TO THE NATIVE FORM OF 2'5'-OLIGONUCLEOTIDES, THE METHOD OF PREPARATION AND THE USE AS REAGENTS IN IMMUNOASSAYS OR FOR BINDING 2'5-OLIGONUCLEOTIDES IN BIOLOGICAL SYSTEMS

[76] Inventors: Julian Gordon, 307 E. Sheridan, Lake Bluff, Ill. 60044; Michael A. Minks, 47 Carroll Avenue, Olivedale, Randburg, South Africa

[21] Appl. No.: 672,266

[22] PCT Filed: Mar. 6, 1984

[86] PCT No.: PCT/EP84/00062

§ 371 Date: Nov. 9, 1984

§ 102(e) Date: Nov. 9, 1984

[87] PCT Pub. No.: WO84/03444

PCT Pub. Date: Sep. 13, 1984

[30] Foreign Application Priority Data

Mar. 10, 1983 [GB] United Kingdom ................ 8306617

[51] Int. Cl.⁴ ...................... C12Q 1/68; G01N 33/53; G01N 33/577; C08G 77/04

[52] U.S. Cl. .......................................... 435/6; 435/4; 435/7; 435/68; 435/240.27; 435/172.2; 435/810; 435/948; 436/501; 436/547; 436/548; 436/808; 530/387; 530/388; 530/808; 530/810; 536/27

[58] Field of Search ............... 530/387, 388, 808, 810; 436/548, 518, 501, 808, 547; 435/948, 810, 240, 241, 172.2, 91, 7, 68, 6, 240.26, 240.27, 102, 103, 108, 110, 4; 536/27

[56] References Cited

PUBLICATIONS

Chemical Abstracts, vol. 99(25), Abstract No. 209018a, 1982.
Chemical Abstracts, vol. 98, Abstract No. 51665b, 1983.
Munns et al., Biochemistry, vol. 21, 2929–2936 (1982).
Cailla et al., Proc. Natl. Acad. Sci. USA, vol. 79, 4742–4746 (1982).

*Primary Examiner*—Christine M. Nucker
*Attorney, Agent, or Firm*—Leydig, Voit & Mayer

[57] ABSTRACT

A new specific antibody to 5'-terminal mono-, di- or triphosphorylated (2'-5')adenyl-adenosine oligonucleotides and a method of producing it have been found. The antibody can be used for the quantitative analysis of the oligonucleotides mentioned above in any one of the well known methods of immunological analysis.

5 Claims, 1 Drawing Sheet

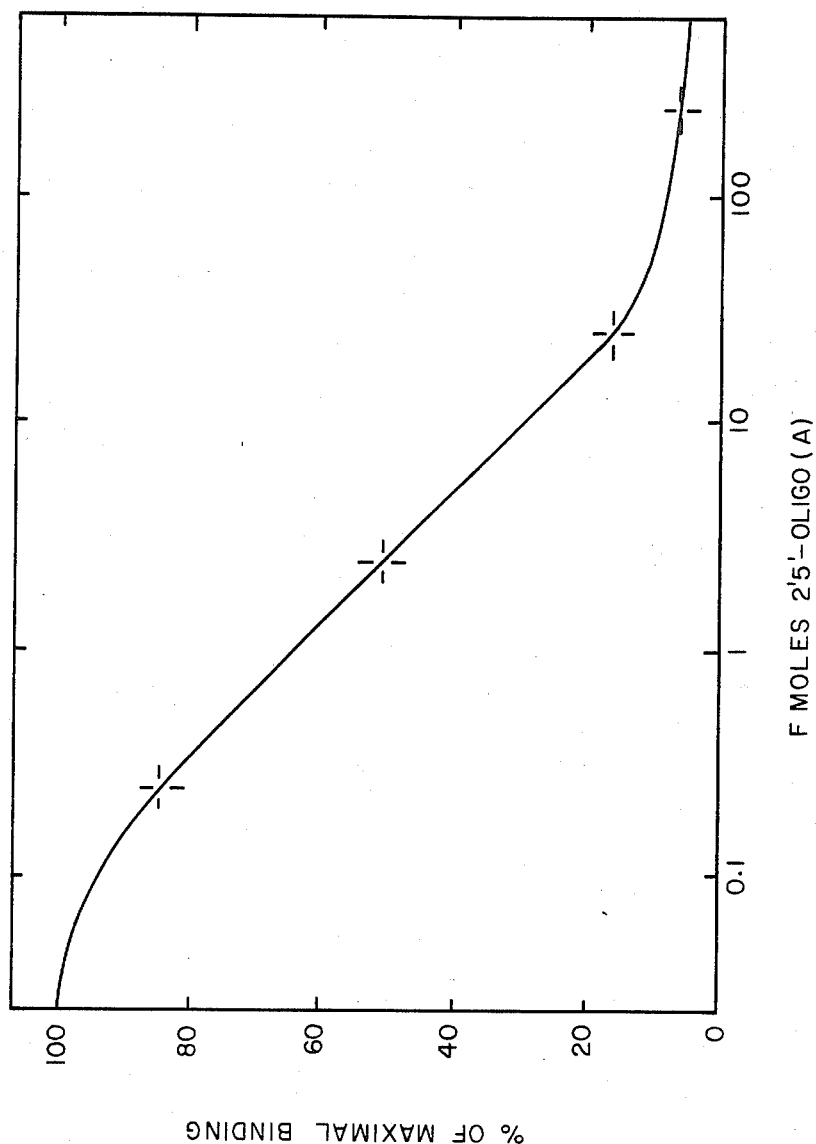

SPECIFIC ANTIBODY TO THE NATIVE FORM OF 2'5'-OLIGONUCLEOTIDES, THE METHOD OF PREPARATION AND THE USE AS REAGENTS IN IMMUNOASSAYS OR FOR BINDING 2'5-OLIGONUCLEOTIDES IN BIOLOGICAL SYSTEMS

The invention relates to a specific antibody to the native form of 2'5'-oligonucleotides; the method for preparing immunogens by coupling oligonucleotides with 2',5' phosphodiester linkages, instead of the common 3'5', and carrying 5' terminal triphosphate to an immunogenic substance in such a way that antibodies of extremely high affinity and specificity can be obtained; and their use as part of highly sensitive immuno-assays for 2'5'-oligo(A) in its native 5'-triphosphorylated form or for 5'-terminal mono- or diphosphorylated (2'-5')adenyl-adenosine oligonucleotides, provided the antibody, has an affinity of 1/100 or more of the affinity to 5'-(phospho)$_3$(adenylyl 2'-5')$_2$ adenosine; or for depleting biological systems of these substances.

Prior Art: The oligomeric series of polynucleotides, known collectively as 5'-triphospho-(adenylyl 2'-5')adenosine, short name 2'5'-oligo(A), have the structure shown below.

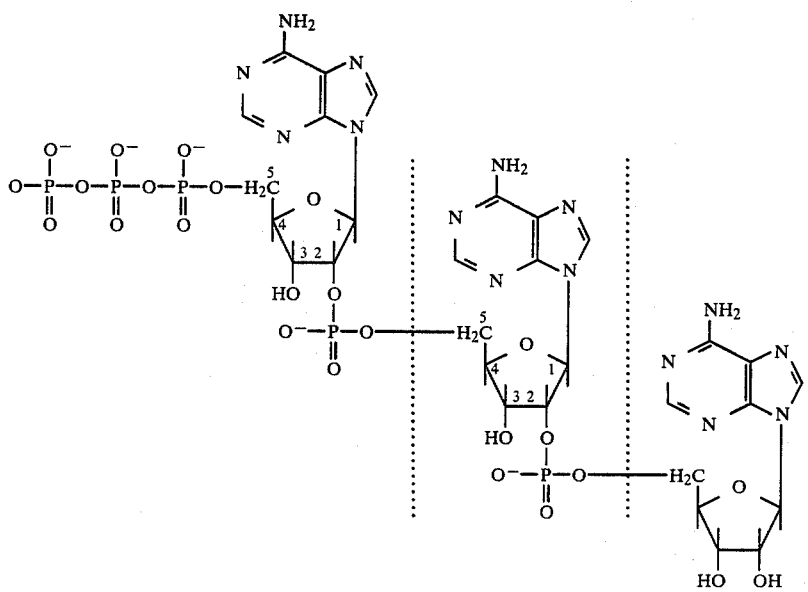

The trimer is shown, and the repeat unit is enclosed in dotted lines.

These compounds have been recently discovered and have aroused a great deal of interest because of their association with interferon, and because they represent an entirely novel class of messenger molecules. The literature concerning this subject has been recently reviewed ("The Interferon Renaissance: Molecular Aspects of Induction and Action". Microbiological Reviews, volume 45, pages 244–266 (1981), by M. Minks and J. Gordon). Most of the inferences concerning the biological action of 2'5'-oligo(A) have been indirect, and relied on the measurements of the enzyme 2'5'-oligo(A) synthetase, which is induced in interferon treated cells. The enzyme can readily be measured as it can be made to function very efficiently in cell extracts in the presence of its activator, double stranded RNA. Such measurements are of potential diagnostic usefulness, since elevated levels are found in a variety of diseases, as well as in response to interferon treatment (Lancet ii, 8745, pages 497–499, 1981 by A. Schattner, G. Merlin, S. Levin, D. Wallach, T. Hahn and M. Revel and Journal of Interferon Research, volume 1, 1981, pages 587–594, by A. Schattner, G. Merlin, D. Wallach, H. Rosenberg, T. Bino, T. Hahn, S. Levin and M. Revel, respectively). Furthermore, a patent application has been filed protecting the use of such enzyme assays (German application DE 30 15 462, by M. Revel, A. Kimchi, L. Schulman and D. Wallach). The usefulness of the assay for 2'5'-oligo(A) synthetase is limited by the fact that it is indirect, and the biological active species is 2'5'-oligo(A) itself. The synthetase does not always faithfully reflect the cellular content of 2'5'-oligo(A), as can be seen from example number 6 of this application.

Some attempts have been made to deal with this problem by developing assays for 2,5'-oligo(A) itself. This can be done by measurement, in extracts of cells, of the ability of the 2'5'-oligo(A) to inhibit protein synthesis or activate an endonuclease (see Methods in Enzymology, volume 79, 1981, pages 199–208, by R. G. Williams, R. E. Brown, C. S. Gilbert, R. R. Golgher, D. H. Wreschner, W. K. Roberts, R. H. Silverman and I. M. Kerr). However, these methods are indirect, cumbersome, not suitable for routine analysis, and involve the use of unstable reagents. The Group of Kerr therefore developed improvements including a radioimmune and a radio-binding assay (See Methods in Enzymology, volume 79, 1981, pages 216–227, by M. Knight, D. H. Wreschner, R. H. Silverman and I. M. Kerr). Their radio-immune assay was dependent on the use of an antibody which was insensitive to the presence of the terminal 5'triphosphate essential for biological activity. Their radio-binding assay was based on the binding of 2'5'-oligo(A) to the above nuclease. This assay has been commercialized by Amersham International, using rabbit reticulocyte lysates as the source of the binding protein. While this assay has a sufficient degree of specificity, it is of limited usefulness because of the use of biochemical preparations which are unstable and need careful handling, because of the presence of degradative enzymes which will preferentially break down the analyte, and because of the finite affinity of the binding protein, which places a limit on the attainable sensitivity. All of the above disadvantages are eliminated in the present invention.

In addition to the antibody of the Kerr group mentioned above, monoclonal antibodies have been prepared ("Monoclonal antibodies to 5'-triphospho-(2'5')adenyl adenosine oligonucleotides" in Proceedings of the National Academy of Sciences of the United States, volume 79, pages 4742-4746, 1982, by H. Cailla, C. LeBorgne de Kauol, D. Roux, M. Delaage and J. Marti), which are also specific for the 2'5' linkage, but not for the presence of the terminal 5'-triphosphate, in spite of the promise of the title. The Kerr group used as immunogen (A2'p)$_2$A, oxidized with periodate to generate a dialdehyde from the 2' terminal ribose, and cross linked this is bovine serum albumin with the aid of cyanoborohydride. Cailla et al prepared di-succinyl 2'5' ApA and cross linked this to human serum albumin with the use of carbodiimide.

Since it is clearly preferable to obtain antibodies specific for the biologically active form of the molecule, it can be concluded that either these groups had earlier attempted this and failed, or else they did not attempt to use the native form of 2'5'-oligo(A) with terminal 5' triphosphate because they anticipated that it would be degraded in the immunization procedure.

According to the invention the new antibody may be prepared by parenterally administering to a vertebrate living animal an immunogen consisting of an immunogenic substance coupled with a fully or partially 3'-ribose and 2'-terminal ribose acylated 2'5'-oligo(A), at time intervals suitable to induce immunization of said animal, gathering blood which contains the resulting specific antibody, and obtaining antiserum from said blood by clotting and optionally centrifugation, or plasma from said blood by addition of anticoagulant and centrifugation.

It is surprising that the antibody preparations obtained contain only a small fraction of molecules with the limited specificity reported in the above two works.

According to the state of the art, nucleotides and oligonucleotides can be protected from phosphodiesterase attack by reagents which form O-ribose adducts. This is because of the need of the phosphodiesterase to form a cyclic structure through a 2' hydroxyl (in the case of the common 3'-5' linked oligonucleotides) as part of its mechanism, as is shown below:

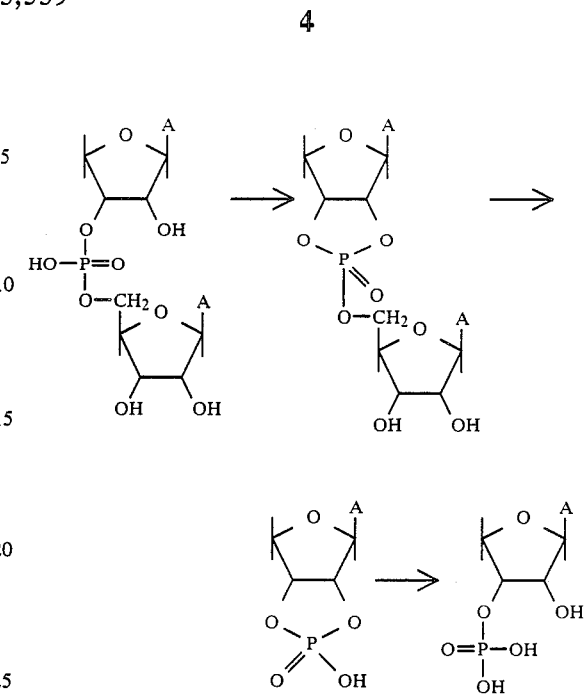

See, for example, "Biochemistry. The chemical reactions of living cells", by D. E. Metzler. Academic Press, New York, 1977, pages 381-382.

BRIEF DESCRIPTION OF THE DRAWING

FIG. 1 percent of maximum binding of antibody as a function of 2'5-oligo(A) added in this competition reaction.

It is surprising that O'ribose modification, which comprises the attachment of the 2'5'-oligo(A) via a linker which promotes its accessibility to the immune system of the animal being immunized, also protects the 5'-terminal triphosphate and permits us to raise antibodies of the specificity revealed in this invention.

The ribose hydroxyls can be acylated with any suitable acidic anhydride, as is well known in the state of the art. See for example the patent of I. Yamamoto (U.S. Pat. No. 4,350,761, 1982) for the preparation of adducts with cyclic AMP. Examples of acidic anhydrides which are suitable for this purpose are e.g. dicarboxylic acid anhydrides.

The preferred form is succinic anhydride, and formula of the resulting e.g. fully succinylated 2'5'-oligo(A) is as shown:

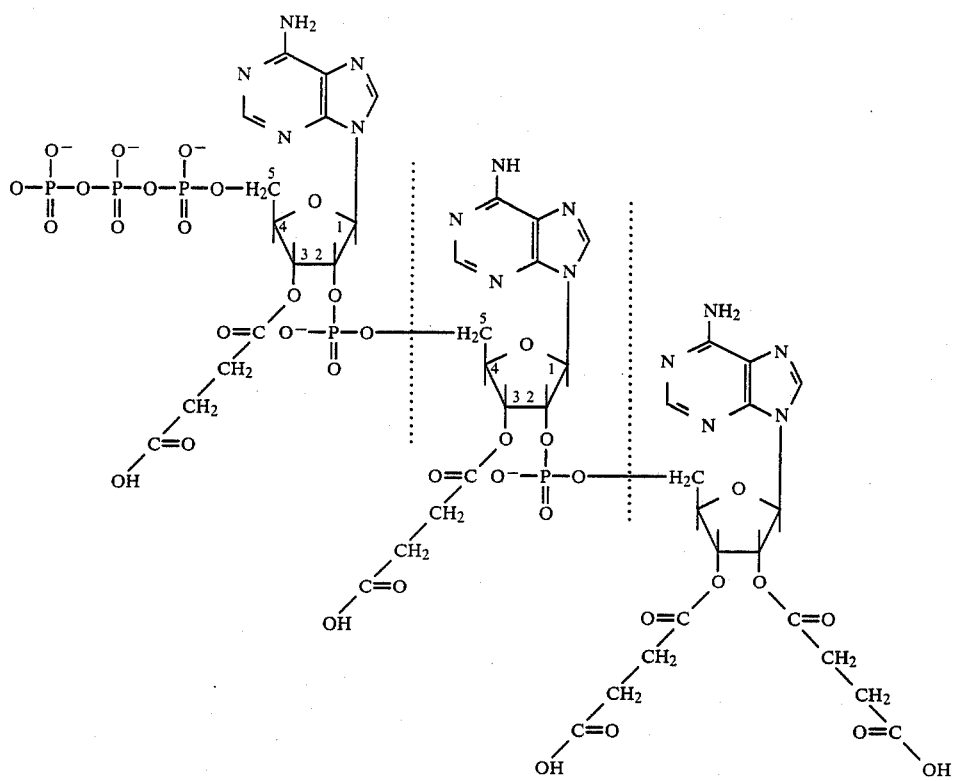

Partially succinylated molecules may also be used.

The acyl 2'5'-oligo(A) derivative is then coupled to a suitable immunogenic substance with a carbodiimide reagent. Suitable immunogenic substances with e.g. proteins, peptides, carbohydrates and phospholipids. The carbodiimide reagent can be 1-ethyl-3-(3'-dimethylamino propyl)carbodiimide, 1-ethyl-3-(3-diethylaminopropyl)-carbodiimide, 1-cyclohexyl-3-(2-morpholinoethyl)-carbodiimide, 1-cyclohexyl-3-(4-diethylaminocyclohexyl)-carbodiimide or N.methyl-N,N'-di-tert-butylcarbodiimidium tetrafluoroborate or other suitable reagent.

After the coupling reaction e.g. with succinic anhydride, the molecule may have the structure below, where R represents e.g. an immunogenic protein coupled via an available amino group:

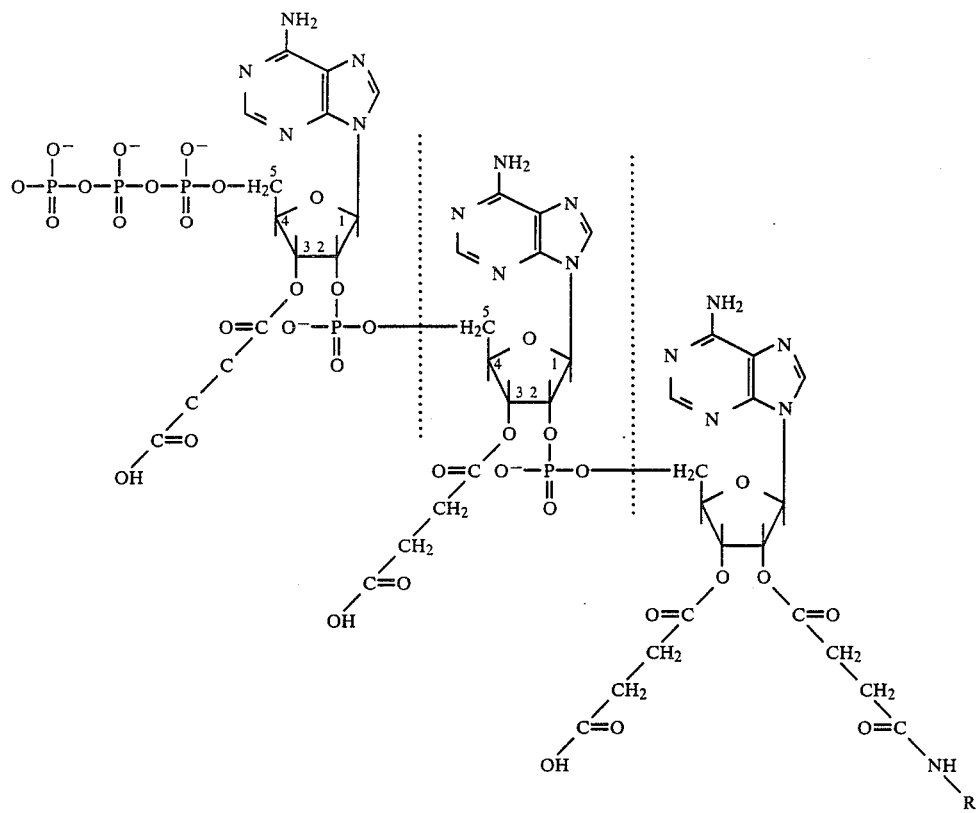

The position of the protein is not defined by the reaction conditions, and in principle, any of the succinyl groups could be reacted, or even combinations, when sterically possible. The exact number and positions of the succinyl groups are also not exactly defined by the reaction conditions, and great heterogeneity is therefore possible. In spite of this, antibodies of great homogenity and specificity are obtained by the conditions of this invention.

The immunogenic protein may be any suitable protein, such as bovine serum albumin, immunoglobulin of the same or other species as used for the immunization, or keyhole limpet hemocyanin. The latter is to be preferred.

Any suitable animal can be used for the immunization, such as sheep, goats, horses, rabbits, rats, mice, chickens, as is commonly used. Rats yield the best results. The titer of the antibody in the serum is optimally assayed by the nitrocellulose binding assay described in the examples, using either [$^3$H]-2'5'-oligo(A) prepared according to a previously published procedure ("Synthesis of 2'5'-oligo(A) in extracts of interferon-treated Hela cells", Journal of Biological Chemistry, volume 254, 1979, pages 5058–5064, by M. A. Minks, S. Benvin, P. A. Maroney and C. Baglioni) or [$^{32}$P]-pCp-2'5'-oligo(A), labelled by means of the T4 polynucleotide kinase reaction, and commercially available from Amersham International. The maximum titer is reached after two booster injections.

The anti-serum so obtained is active at high dilutions (>50,000-fold), is stable to freezing, thawing and lyophilization, and can thus be packaged, shipped or stored with no difficulty. The serum is also totally free of any 2'5'-oligo(A) degrading activity, especially at the high dilutions used in the assays. This is in contrast to the cell extracts used in the radio-binding assay mentioned above.

The 2'5'-oligo(A) can be extracted from biological material by any of the commonly used extraction procedures for making cell-free extracts, provided care is taken to avoid either degradation or re-synthesis under the extraction conditions. Homogenization with buffered saline may be used, but acid extraction is to be preferred. Optimally, cold trichloroacetic acid extraction is used, preferably in the range 5–20%. The trichloroacetic acid can then be removed by ether extraction, or preferably by freon-octylamine extraction according to a published procedure ("Extraction procedures for use prior to HPLC nucleotide analysis using microparticle chemically bonded packings", Journal of Chromatographic Science, volume 15, 1977, pages 218–221, by S-C. Chen, P. R. Brown and D. M. Rosie). This procedure is excellent for all kinds of biological materials, including cultured cells, organs, tissues or any biological fluids such as blood, urine, cerebrospinal fluid, etc. The extract may be lyophilized to reduce the volume and remove extraneous volatile material. If desired, an additional step of chromatography (High Performance Liquid Chromatography or conventional column chromatography) may be used. Stepwize chromatography on diethylaminoethyl cellulose is especially simple and useful for removal of the cellular ATP, which may be at concentrations $\geq 10^6$-fold the analyte concentration.

According to the invention the resulting specific antibody is used for the assay of 5'-terminal mono-, di- or tri-phosphorylated (adenylyl 2'-5')$_n$ adenosine in biological material by any commonly used methods of immunological analysis, namely by determination of free or bound ligand or determination of free or bound antibody or determination of antibody-ligand interaction by means of a signal which is modulated by the antibody-antigen reaction. For instance, this can be done either determining the reduction of binding of a known highly radioactive ligand, such as [$^{32}$P]-pCp-labelled 2'5'-oligo(A), after binding the antibody-ligand complex to a solid support, such as nitrocellulose. The ligand can be labelled with any suitable radioactive isotope. It is also possible to label the ligand with a fluorescent, enzymatic or luminescent moiety. The assay can also be of the sandwich type, where antibody of one specificity is bound to a solid support, used to bind the unknown analyte, and detected with an antibody of second specificity. Of this pair forming the sandwich, one may be the specific antibody defined by the present invention, and the other may be of the type described by the groups of Kerr or Cailla described above, or directed against the adenosine, as described by Erlanger and Beiser (Proceedings of the National Academy of the United States, volume 52, 1964, pages 68–74). The label need not be in the ligand for any of the above assays, but may be in one of the antibodies, or in a second antibody directed against one of the primary antibodies, as is well-known in the art.

The preferred form of assay for detection of fmoles of 5'-terminal mono-, di- or tri-phosphorylated (adenylyl-2'-5')$_n$ adenosine in extracts from biological material is the competition binding assay already mentioned, where the unknown is mixed with a known amount of known radioactive ligand, incubated with a dilution of the antibody, mixed with suitable buffer, poured over nitrocellulose in a filtration apparatus, and the excess unbound ligand removed by washing, and counting in a scintillation counter. The assay is fast and simple, and the reaction is complete in a few minutes at reduced temperature. The assay by reduction of binding of the labelled 2'5'-oligo(A) is as shown in FIG. 1.

Even more sensitive assays can be constructed with the use of labelled antibodies.

The main application of such assay at present lie in the field of research into the biochemistry of interferon action, and in the biochemistry of action of hormones, lymphokines, growth factors etc. The wide importance of 2'5'-oligo(A) is evidenced by the fact that 2'5'-oligo(A) synthetase is induced in a variety of systems other than interferon such as in the differentiating chick oviduct following estrogen withdrawal, as described ("2-5A synthetase: assay, distribution and variation with growth hormone status", Nature, volume 278, 1979, pages 471–473, by G. R. Stark, W. J. Dower, R. T. Schimke, R. E. Brown and I. M. Kerr), or in Friend Erythroleukemia transformed mouse erythroblasts, triggered into differentiation by various reagents ("Increased levels of interferon-induced (2'-5') oligo-isoadenylate synthetase in mature lymphocytes and in differentiated Friend erythroleukemic cells", Journal of Interferon Research, volume 1, 1981, pages 559–569, by A. Kimchi). Since the real action of the synthetase depends on its induction and on the simultaneous presence of its activator double stranded RNA, such information is of limited usefulness. In the examples which follow, we demonstrate using the methods of this invention, that indeed, in interferon treated HeLa cells, with a high level of 2'5'-oligo(A)-synthetase, the 2'5'-oligo(A) is unaltered from the basal level, while in the differentiating Friend Erythroleukemia cells, there is a parallel increase in synthetase and 2'5'-oligo(A).

An additional use for the antibody made according to the methods of the present invention is as a 5'-terminal mono-, di- or tri-phosphorylated (adenylyl 2'-5')$_n$ adenosine chelating agent. It can be added to cell-free protein synthesizing systems, and rescue them from the inhibition by added or endogenous 2'5'-oligo(A). It can also be used therapeutically, where it is desired to reduce the cellular levels of 2'5'-oligo(A).

Since 2'5'-oligo(A) is such an important newly discovered signal molecule, it is anticipated that the methods of this invention will lead to the discovery of multitudes of novel uses in research, diagnosis and therapy.

Diagnostic applications of the 2'5'-oligo(A) synthetase for viral infection, leukemias, auto-immune and connective tissue diseases have already been explored by the group of Revel in the publication in Lancet (see above) and for monitoring interferon treatment, in the Journal of Interferon Research (also mentioned above). Wide applications of assays for the biologically active molecule itself, which yield more direct and relevant information by simpler methodology, can be anticipated in all of the above circumstances.

The more sensitive assays for 2'5'-oligo(A) provided by this invention also permits more sensitive assays for the enzyme 2'5'-oligo(A) synthetase. Further, since the enzyme requires double standed RNA for activity, this also provides an extraordinarily sensitive assay for double stranded RNA. With this method, it is therefore also possible to determine the small amounts of double stranded RNA in biological material which would be necessary for the activation of the 2'5'-oligo(A)-synthetase.

In order to explain more fully the invention, the following examples are set forth, it being understood that these examples are not intended to limit the scope of the invention.

EXAMPLE 1

Preparation of the specific antibody to the native form of 2'5'-oligonucleotides The 2'5'-oligo(A) itself is prepared in quantity using interferon treated Hela cell extracts themselves prepared by published methodology (Minks et al., J. Biol. Chem., 254, 1979, pp 5058–5064). The 500 ml reaction mixture contains 5 mM ATP, 3 mM fructose-1,6-biphosphate, 100 mM KOAc, 25 mM Mg(OAc)$_2$, 10 mM HEPES/KOH, pH 7.4, 1 mM dithiothreitol, 10 $\mu$g/ml poly(rI).poly(rC) and 1 mg/ml of post-mitochondrial supernatant from interferon treated Hela cells. The mixture is incubated for 15 hr at 30° C., at which stage conversion of ATP to 2'5'-oligo(A) is >30%. The reaction is terminated by boiling for 3 min and denatured proteins are removed by centrifugation or filtration.

The 2'5'-oligo(A) is separated from ATP and other mononucleotides by ion exchange chromatography on diethylaminoethylcellulose (DEAE cellulose). The clarified boiled extract is diluted with an equal volume of distilled water, and loaded on to a DEAE cellulose column equilibrated with 50 mM NaCl or KCl in 10 mM Tris HCl, pH 7.6, or with 50 mM NH$_4$HCO$_3$ or triethylamine bicarbonate pH adjusted to 7.6. The column is loaded with 100 A$_{260}$ units of the extract per ml of packed column volume. Typically, a 400 ml column is used. The oligonucleotides are eluted with a salt gradient from 50 to 400 mM of the selected salt, using 4 l of gradient. The ATP elutes first, followed by the 2'5'-oligo(A) oligomers in order of increasing polymeric size. This can be determined from the ultraviolet absorption profile of the column effluent. The desired fractions are pooled, and the 2'5'-oligo(A) desalted by precipitation with 5 volumes of acetone, or by lyophilization if the volatile buffer is used.

The 2'5'-oligo(A) is succinylated in a reaction mixture containing 10% (v/v) triethylamine, 50 mg/ml succinic anhydride and 5 mM 2'5'-oligo(A). Typically, 5 ml reaction volume is used. Incubation is at room temperature for 10 min. The nucleotides are precipitated with 5 volumes of acetone, followed by de-salting on a column of Sephadex G25.

The succinylated 2'5'-oligo(A) is coupled to keyhole limpet hemocyanin (from Calbiochem) as follows. The hemocyanin is dissolved at 10 mg/ml in a 10 mg/ml solution of succinyl 2'5'-oligo(A), and 1-ethyl-3(3'-dimethylaminopropyl)carbodiimide. HCl is added gradually while readjusting the pH to 5.5 with KOH. The condensation reaction is allowed to proceed overnight at room temperature in the dark. The conjugate is freed from reactants by dialysis against 0.15M NaCl, 0.01M potsassium phosphate buffer, pH 6.8 (PBS) for 2 days at 4° C. with at least 4 buffer changes. The degree of coupling is verified by the spectral alteration before and after coupling; using the $A_{260}$ value as a measure of the 2'5'-oligo(A) content; or by radioactivity, by inclusion of a small portion of radioactive 2'5'-oligo(A) in the original coupling reaction. The degree of substitution obtained is in the range 80–100 moles of oligonucleotide per mole of protein.

Successful immunization of rats, mice or rabbits is obtained with the following procedures. Primary injections are with succinyl-2'5'-oligo(A) conjugate in an equal volume of Complete Freund's Adjuvant and boosters are in an equal volume incomplete Freund's Adjuvant. The conjugate is at 1 mg/ml in PBS. Rats are injected intraperitoneally with 0.5 mg of conjugate and boosted with the same amount at two weekly intervals. Mice are immunized similarly, but with 100 μg per injection. Rabbits are immunized by subdermal injection of 1 mg of conjugate at five sites on the back, and boosted with 0.75 mg at three weekly intervals. Rats and mice are bled by the tail vein and rabbits by the ear vein 10 days after the previous injection. Rats are preferably 150–200 g females, mice 30 g and rabbits 3 kg.

EXAMPLE 2

Titer of specific antisera

The titers of the antisera are determined from the reciprocal of the dilution which gives 50% retention of the radioactivity to a nitrocellulose filter. The antiserum dilution is incubated in 25 μl of 20 mM KOAc, 10 mM HEPES-KOH, pH 7.4, 1.5 mM Mg(OAc)$_2$ containing 1 mg/ml bovine serum albumin (BSA) and 5–6000 cpm of [$^{32}$P] terminally labelled 2'5'A tetramer pCp (Amersham International: specific activity, approximately 3000 Ci/mmole). After incubation at 0° for 1 hr, the mixtures are diluted with 3 ml of ice cold 90 mM KCl, 20 mM Tris-HCl, pH 7.6 and passed through 25 mm discs of nitrocellulose (Millipore, type HAWP, 0.45μ) with a filtration apparatus. The filters are washed with a further 2 portions of the same buffer, and retained radioactivity counted by Cerenkov radiation in a scintillation counter. Maximal titers of 50,000, 5,000 and 1,000 are usually obtained for rats, mice and rabbits, respectively, and after the second booster injection.

EXAMPLE 3

Competitive binding assays

In the simple radio-immune assay described in Example 2, the unknown is determined by dilution of the radioactivity bound from the constant amount of known radioactive probe. Other related substances will bind to the antibody more or less well, depending on their relative affinities, and may thus also give a reduction in the bound radioactivity. This inhibtion is a measure of the affinity of the related compound for the antibody, and will also indicate to what extent such compounds might interfere with the assay, if present in the material being analysed. The concentration of the related substance giving 50% inhibition of the binding of the radioactive probe is used as a measure of its relative affinity. A collection of 2'5'-adenylates and related compounds were prepared as follows. The dimer, trimer, tetramer and pentamer were obtained from the DEAE-cellulose fractionation of example 1. The tetramer was partially digested with bacterial alkaline phosphatase and the products separated by high performance liquid chromatography on a Partisil SAX column (Whatman), with 10 mM potassium phosphate buffer, pH 6.8, 20% ethanol and a gradient from 10 to 500 mM KCl. Acetyl and succinyl derivatives of the tetramer were obtained by reaction with acetic and succinic anhydride, according to the method of Example 1. Other compounds were from commercial sources. The amounts of the various compounds which gave 50% inhibition of the maximal binding of the [$-^{32}$P]-labelled probe (see Example 2) are listed below.

|  | fmoles |
| --- | --- |
| pppA(2'p5'A)$_4$ | 2.5 |
| pppA(2'p5'A)$_3$ | 2.5 |
| pppA(2'p5'A)$_2$ | 2.5 |
| pppA(2'p5'A) | 850 |
| 2-O—succinyl pppA(2'p5'A)$_3$ | 2,0 |
| 2-O—acetyl pppA(2'p5'A)$_3$ | 2.5 |
| ppA(2'p5'A)$_3$ | 12 |
| pA(2'p5'A)$_3$ | 25 |
| A(2'p5'A)$_3$ | 500 |
| A(2'p5'A)$_2$ | 500 |
| A(3'p5'A)$_2$ | 2,500,000 |
| pA(3'p5'A)$_3$ | 250,000 |
| AMP, ADP, ATP, GTP, CTP, UTP, NADH, pCp | >3,000,000 |

The assay is therefore able to detect fmole amounts of oligonucleotides with appropriate specificity. The affinity of the antibody is so high that the same results will be obtained with any reaction volume between the 25 μl specified in the preceeding example and 1 ml. The affinity of the antibody is ~$10^{12}$ M$^{-1}$. The affinity of the antibody for the 5'-phosphorylated forms of 2'5'-oligo(A) is 20–200 times that for the de-phosphorylated core. This supports the concept that the antibody is specific for 5'-phosphorylated 2'5'-oligo(A).

EXAMPLE 4

Preparation of extracts for 2'5'oligo(A) radioimmunoassays

This is an example for cells growing in culture, but is universally applicable to any biological material: cell cultures, organs, tissues, bodily fluids such as blood, urine, cerebrospinal fluids, milk or any other suitably available material. Cells in a petri dish are rapidly washed with buffered saline (this step is dispensed with in the case of bodily fluids), then enough ice cold 5% trichloracetic acid (TCA) to cover the layer of cells (3 ml for a 7 cm diameter petri dish) and the dish is kept on ice for 5 min. The TCA and detached cells are removed and centrifuged to remove the insoluble material, and the dish and pellet are re-extracted with a similar volume of 5% TCA and the supernatants pooled. Alternatively, in the case of a cell suspension culture, the cells are pelleted by centrifugation at room temperature, the cells resuspended in a volume of buffered saline equal to the volume of the pellet, and approximately 10 volumes of 5% TCA are added. The insoluble material is removed by centrifugation and the pellet extracted with ½ the previous volume of 5% TCA. The supernatants are pooled. All operations with TCA are performed between 0° C. and 5° C. The pooled supernatants are freed of TCA by extraction with an equal volume of 30% (v/v) tri-N-octylamine in Freon 113 (Dow Chemicals). The upper aqueous phase is collected and the Freon phase re-extracted with ½ the preceeding volume of distilled water. Since biological material may contain ATP in the mM range, and it is desirable to measure 2'5'-oligo(A) in the nM range, it may be desirable to remove such $10^6$-fold excess of ATP, which might interfere with the assay. The ATP and other nucleotides which might interfere with the assay may then be removed chromatographically with DEAE cellulose (Whatman DE-52) equilibrated with 125 mM $NH_4HCO_3$ (pH 7.8). The loading ratio is the same as for the preparative columns of example 1, but microcolumns of 200 μl are optimal for this analytical scale. The column is washed with 15 ml of the same buffer to remove the ATP and other unbound material. The 2'5'-oligo(A) is eluted with 2 ml of 0.5M $NH_4HCO_3$, and the samples are lyophilized after addition of 1/10th volume of ethanol. The samples may be stored indefinitely in anhydrous form and re-dissolved with suitable volumes of solvent for the radio-immuno assay as described in example 3.

EXAMPLE 5

Determination of 2'5'oligo(A) levels in differentiating cells

Friend mouse erythroleukemia cells can be induced to differentiate and become erythropoietic under the influence of a variety of reagents, especially dimethylsulfoxide. Such cells are also known to produce the enzyme 2'5'-oligo(A) synthetase. Before the method of the present invention, it was not possible to determine the 2'5'oligo(A) directly in these cells. The determination is described in this example. The Friend cells (clone FBU or N46AP) are grown in Dulbecco's modified Eagle's Medium containing 10% fetal calf serum, 2% (v/v) dimethylsulfoxide for FBU or 1.4% (v/v) DMSO for N46AP and 1 mM glutamine. The cells are diluted with the same medium daily to maintain a density of $5.10^5$ cells per ml. At various times, 30 ml cultures are collected and processed as described in the preceeding example. The lyophilized material is dissolved in the buffer corresponding to the reaction mixture for the assay, as in example 2, but containing 0.1 mg/ml of bovine serum albumin. The 2'5'-oligo(A) content is determined from the reduction of the binding of the [$^{32}$P] labelled probe as in example 2 and 3. The following results are obtained:

| Cell line | Days post-DMSO | 2'5'-oligo(A) (fmoles/$10^6$ cells) |
|---|---|---|
| FBU | 0 | 2.6 |
| | 1 | 28 |
| | 2 | 28 |
| | 4 | 20 |
| N46AP | 0 | 7.5 |
| | 1 | 7.8 |
| | 2 | 4.3 |
| | 3 | 17.5 |
| | 5 | 63 |
| | 6 | 53 |

In the case of the N46AP cell line, there is a delay between the first appearance of the 2'5'-oligo(A) synthetase and the 2'5'-oligo(A) itself, while in the FBU line the two go in parallel.

This example demonstrates for the first time the possibility of determination of 2'5'-oligo(A) in cells not treated with interferon.

EXAMPLE 6

Determination of 2'5'-oligo(A) in interferon treated Hela cells

Cultures of Hela cells respond very well to interferon in the induction of 2'5'-oligo(A) synthetase (see example 1). The basal 2'5'-oligo(A) itself was too low to be measured by other methodology. This example demonstrates such measurement. Hela cells of the S3 line are cultivated in the presence of 20 units/ml of interferon α2 for 24 hrs. The cells are centrifuged and processed according to example 4. The 2'5'-oligo(A) synthetase is assayed by methods well described in the literature in parallel cultures. The synthetase increases 10-fold over the basal level, while the 2'5'-oligo(A) itself remains at the basal level of 0.45±0.15 nM. This shows that 2'5'-oligo(A) synthetase levels are not invariably indicative of the biologically active species, 2'5'-oligo(A).

EXAMPLE 7

Enhanced sensitivity assay for 2'5'-oligo(A) synthetase

Because of the extremely efficient reaction condition of cell-free systems, it is possible to assay low levels of 2'5'-oligo(A) synthetase. However, it is sometimes desirable to measure low levels from extremely small amounts of precious starting material. By coupling the extremely sensitive measurement of 2'5'-oligo(A) according to the methods of the present invention, with the enzymatic assay for 2'5'-oligo(A) polymerase, the enzyme can be determined with $10^5$-fold higher sensitivity than was previously possible. In the example, Swiss mouse 3T3 fibroblast cells are stimulated into a cell cycle by a variety of hormones and factors (for literature on this subject see the article "Criteria for the establishment of the biological significance of ribosomal protein phosphorylation" in Current Topics in Cellular Regulation, volume 21, 1982, pages 89-99, by J. Gordon, P. J. Nielsen, K. L. Manchester, H. Towbin, L. Jimenez de Asua and G. Thomas). Quiescent 3T3 cells in Dulbecco's modified Eagle's minimal medium and 10% fetal calf serum, in 10 cm Petri dishes are treated overnight with various reagents. On the following day the monolayers are washed with phosphate buffered physiological saline and the cells suspended in 2 ml per dish of the same. The cells are centrifuged at 800 g for 5 min and the packed cells treated with twice the pellet volume of 10 mM HEPES-KOH, pH 7.4, 20 mM KOAc, 1.5 mM Mg(OAc)$_2$, 2 mM DTT, 0.1% (v/v) triton X-100, and 10% glycerol, for 10 min at 0°. The cell debris are removed by centrifugation at 30,000 g for 10 min and the supernatant is used as the source of 2'5'-oligo(A) polymerase. The supernatant (40 μl, 30 A$_{260}$) is mixed with 100 μl of poly(rI).poly(rC)-agarose beads (P-L. Biochemicals) and 100 μl of 20 mM Tris-HCl pH 7.6, 225 mM KOAc, 12 mM Mg(OAc)$_2$, 1 mM dithiothreitol, 10 μM phenylmethylsulfonylchloride and 10% glycerol. The non-adsorbed material is removed after centrifugation to pellet the beads and the agarose is washed three times with 200 μl aliquots of the latter buffer. The 2'5'-oligo(A) synthesis is allowed to proceed overnight in the presence of 50 μl of the latter buffer supplemented with 10 mM ATP containing 500,000 cpm of [$^3$H]-ATP. The reaction is terminated by addition of 150 μl of 90 mM KCl, 20 mM Tris-HCl pH 7.6. The beads are removed by centrifugation and the supernatant divided into 2 portions, one for a conventional assay and the second for the radio-immune assay of the reaction product. One portion (198 μl) is analysed for conversion of the ATP to 2'5'-oligo(A) from the retention of radioactivity on an analytical DEAE cellulose column (see example 4). The other portion (2 μl) is diluted in the range 250 to 10,000-fold and the 2'5'-oligo(A) determined by the radioimmune assay (see example 3). The following results are obtained.

| Treatment | [$^3$H]—ATP → [$^3$H]—2'5'-oligo(A) cpm/assay | Radio-immune assay for 2'5'-oligo(A), pmoles/assay |
|---|---|---|
| None | 556 | 50 |
| +10 μM prostaglandin F2α | 632 | 100 |
| +100 u/ml interferon | 4109 | 2000 |
| Background of assay | (197) | 0 |

With radioactive ATP, more than 10$^7$ cells must be extracted to obtain a significant signal. The sensitivity is limited by the high Km of the enzyme (c. 1 mM) and the background of the assays itself. In general, it is difficult to discriminate lower than 1/10$^4$ of the input ATP. The antibody assay improves both the sensitivity and the selectivity. The discrimination factor between 2'5'-oligo(A) and ATP is ca. 10$^6$-fold, and this can be enhanced to 10$^8$-fold with a DEAE cellulose column step. The minimal amount of 2'5'-oligo(A) to give a signal is in the fmole range, considerably lower than that needed to detect the 2'5'-oligo(A) in the above table. The enhanced sensitivity of the radio-immune assay is thus 10$^5$-fold. It thus permits the use of smaller amounts of biological material, biological material with very low activity, or the measurement of smaller amounts of material which activitates the synthetase, than would otherwise be possible.

EXAMPLE 8

Non-isotopic immuno-assays for 2'5'-oligo(A)

Great developments have been made in recent years in easier and safer alternatives to radio-immunoassay techniques. For example, such methods have been developed which are of great simplicity and sensitivity, based on nitrocellulose as a solid support and peroxidase-conjugated antibodies as label (see "A dot-immunobinding assay for monoclonal and other antibodies", Analytical Biochemistry, volume 119, 1982, pages 142–147, by R. Hawkes, E. Niday and J. Gordon and U.K. Patent Application No. 2099578 "New Kits for Immunological Analysis", 1981, by J. Gordon, R. Hawkes, E. Niday and H. Towbin). Conjugated 2'5'-oligo(A) is prepared with bovine serum albumin instead of hemocyanin according to example (1). This is diluted to 0.2 mg/ml in TBS (0.01M Tris-Cl, pH 7.6, 0.15M NaCl), 1 mg/ml BSA. Rat anti-serum against 2'5'-oligo(A) prepared according to example (2) is diluted 1:10,000 in TBS, 1 mg/ml BSA, 0.01% Nonidet P40 (Shell Chemicals). Standard and unknown samples are diluted into 1 ml portions of the diluted anti-serum, and incubated for 1 hr at room temperature. These are then added to the nitrocellulose and incubated for a further 2 hrs at room temperature, with gentle agitation. The strips are then washed with TBS and incubated a further 2 hrs in 1 ml of peroxidase conjugated rabbit anti-rat immunoglobulins (DAKO, Copenhagen), diluted 1:500 in TBS, 1 mg/ml BSA, 0.01% Nonidet P40. The strips are then washed again with TBS and incubated in 1 ml 0.6 mg/ml chlornaphthol and 0.01% H$_2$O$_2$ in TBS for 15 min. The inhibition of the color reaction is then taken as a measure of the amount of unknown 2'5'-oligo(A). A reduction of 50% is obtained with 100 fmoles of 2'5'-oligo(A).

EXAMPLE 9

Kits for assay of 2'5'-oligo(A)

Such kits may consist of two parts: (a) for the extraction and (b) for the performance of the assay itself. These are provided either together or separately.

(a) comprises materials for carrying out the procedure of example (4) in a stable, packaged form. Trichloracetic acid is provided in packs containing 5 g, to be made up to 100 ml with distilled water. Physiological saline pH 6.8 is provided in packs containing 0.88 g NaCl, 0.14 g KH$_2$PO$_4$ and 0.23 g K$_2$HPO$_4$.3H$_2$O, to be made up to 100 ml with distilled water. Freon 113 and tri-N-octylamine are provided in ampoules of 35 and 15 ml, respectively, which, when mixed, provide the non-aqueous phase for the extraction of the trichloracetic acid. The provision of the latter two ingredients as part of a kit is especially useful as they are not generally available in biochemical or clinical laboratories. The latter volumes provide enough for approximately 50 assays. Disposable microcolumns are made by packing 0.2 ml of DEAE cellulose (Whatman DE52) equilibrated with 125 mM NH$_4$HCO$_3$ and 0.05% NaN$_3$ as preservative, in disposable polypropylene 2 ml Econocolumns (from Biorad Corporation). These are packed in the kit with the top sealed with the stopped provided and the bottom with a luer fitting. NH$_4$HCO$_3$ is provided in packs of 9.88 g, which can be made up to 1 liter for the column wash buffer or to 250 ml for the elution buffer.

(b) For a radio-immune assay, the kit contains 2'5'A tetramer triphosphate [$^{32}$P]Cp 3' end labelled, 25 μCi, as supplied by Amersham International, rat antiserum against 2'5'-oligo(A) prepared as in example (1). The antiserum is diluted 50,000 fold in 20 mM KOAc, 10 mM HEPES-KOH, pH 7.4, 1.5 mM Mg(OAc)$_2$, 1 mg/ml bovine serum albumin, divided into 1.25 ml portions and lyophilized. Each portion provides material for 50 assays following reconstitution. Washing buffer is made from portions of 0.67 g KCl, 0.24 g Tris and 1.9 ml 1N HCl. The mixture is lyophilized and packed. Each pack provides 100 ml of wash buffer when reconstituted with distilled water. Alternatively, the probe may be made by conjugation of succinyl 2'5'-oligo(A) with tyrosine by methods known for cyclic AMP (see Cailla, H. L. & Delaage, M.A. in Analytical Biochemistry 48 (1972), page 62), and labelled with [$^{125}$I] by the chloramine T method.

The kit may also be assembled for enzyme-based immuno-assay. In its simplest form, multi-well dishes are provided with 3 mm×3 mm squares of nitrocellulose (Millipore type HAWG) in each well. The squares are prepared with 0.5 μl of 1:50 dilute antiserum and saturated with 10% horse serum as in example (8). The remaining components of the kit are as described in U.K. Patent Application No. 2099758.

We claim:

1. A specific antibody to 5'-terminal mono-, di- or triphosphorylated (2'-5')adenyl-adenosine oligonucleotides of formula 5'-(phospho)$_m$(adenylyl 2'-5')$_n$ adenosine with m being an integer of from 1 to 3 and n being an integer of from 2 to 50, provided that said antibody has a greater affinity for the 5'-phosphorylated than the 5'-hydroxyl form of said (2'-5')adenyl-adenosine oligonucleotides.

2. A method for the assay of 5'-terminal mono-, di- or tri-phosphorylated (adenylyl 2'-5')$_n$ adenosine, in biological materials or extracts therefrom, comprising contacting the antibody of claim 1 in any one of the three following methods of immunological analysis: (a) by determination of free or bound ligand or (b) determination of free or bound antibody or (c) determination of antibody-ligand interaction by means of a signal which is modulated by the antibody-antigen reaction.

3. The method according to claim 2 in which the ligand is labelled with a radioactive, enzyme, fluorescent, enzyme-substrate, co-enzyme, enzyme prosthetic group or luminescent label, wherein the non-labelled species may be bound to a solid support.

4. A method for depleting biological systems of 5'-terminal mono-, di- or triphosphorylated (adenylyl 2'-5')$_n$ adenosine wherein n is an integer of from 2 to 50 comprising contacting the antibody of claim 1 with said biological system.

5. Kit for the quantitative analysis of 5'-(phospho)$_m$-(adenylyl 2'-5')$_n$ adenosine wherein m and n have the meanings as in claim 1 comprising in separate packages:
   (a) a labelled 2'5'-A tetramer triphosphate;
   (b) a diluted antiserum against 2'5'-oligo(A); and
   (c) components suitable for preparing biological samples.

* * * * *